(12) United States Patent
Iseberg et al.

(10) Patent No.: US 9,191,761 B2
(45) Date of Patent: Nov. 17, 2015

(54) HEARING TESTING PROBE WITH INTEGRATED TEMPERATURE AND HUMIDITY SENSORS AND ACTIVE TEMPERATURE CONTROL

(71) Applicants: Steve Iseberg, Hoffman Estates, IL (US); Steve Viranyi, Palatine, IL (US); Andrew Dale, Mount Prospect, IL (US); Jerrold S. Zdenek, Deer Park, IL (US)

(72) Inventors: Steve Iseberg, Hoffman Estates, IL (US); Steve Viranyi, Palatine, IL (US); Andrew Dale, Mount Prospect, IL (US); Jerrold S. Zdenek, Deer Park, IL (US)

(73) Assignee: ETYMOTIC RESEARCH, INC., Elk Grove Village, IL (US)

(*) Notice: Subject to any disclaimer, the term of this patent is extended or adjusted under 35 U.S.C. 154(b) by 454 days.

(21) Appl. No.: 13/753,320

(22) Filed: Jan. 29, 2013

(65) Prior Publication Data
US 2013/0195299 A1    Aug. 1, 2013

Related U.S. Application Data

(60) Provisional application No. 61/592,359, filed on Jan. 30, 2012.

(51) Int. Cl.
*A61B 5/00* (2006.01)
*H04R 29/00* (2006.01)
*A61B 5/12* (2006.01)

(52) U.S. Cl.
CPC ............... *H04R 29/00* (2013.01); *A61B 5/121* (2013.01); *A61B 5/7203* (2013.01); *A61B 2560/0252* (2013.01); *A61B 2560/0257* (2013.01)

(58) Field of Classification Search
CPC ........................................................ H04R 29/00
USPC ............ 600/559, 549, 547; 381/175, 314, 74; 73/862.68
See application file for complete search history.

(56) References Cited

U.S. PATENT DOCUMENTS

| | | | | |
|---|---|---|---|---|
| 6,126,614 | A * | 10/2000 | Jenkins et al. | 600/549 |
| 2007/0071260 | A1* | 3/2007 | Mullenborn et al. | 381/175 |
| 2010/0191144 | A1* | 7/2010 | Zoth et al. | 600/559 |
| 2010/0220879 | A1* | 9/2010 | Feilner et al. | 381/314 |
| 2013/0114823 | A1* | 5/2013 | Kari et al. | 381/74 |
| 2013/0204157 | A1* | 8/2013 | Clark et al. | 600/547 |

* cited by examiner

*Primary Examiner* — Brian Szmal
(74) *Attorney, Agent, or Firm* — McAndrews, Held & Malloy, Ltd.

(57) ABSTRACT

Certain embodiments provide a hearing testing system. The hearing testing system includes a transducer and an environmental sensor coupled with an acoustic channel. The environmental sensor is configured to measure environmental conditions of the acoustic channel. The hearing testing system includes a processor. The processor is configured to receive the environmental conditions from the environmental sensor. The processor is configured to apply, based on the measure environmental conditions, correction data to a transducer response to generate a corrected transducer response. In certain embodiments, the processor is configured to control a heating element based on a measured temperature to maintain a pre-defined temperature, or range of temperatures, at a testing probe.

16 Claims, 9 Drawing Sheets

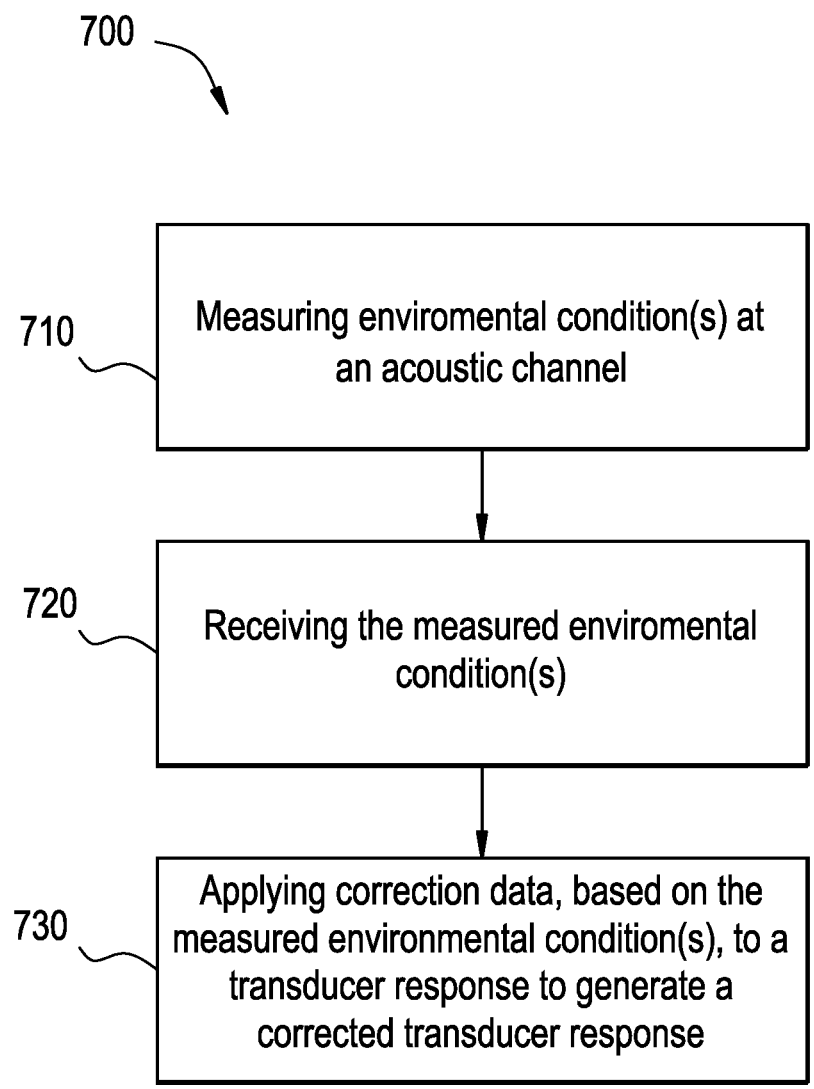

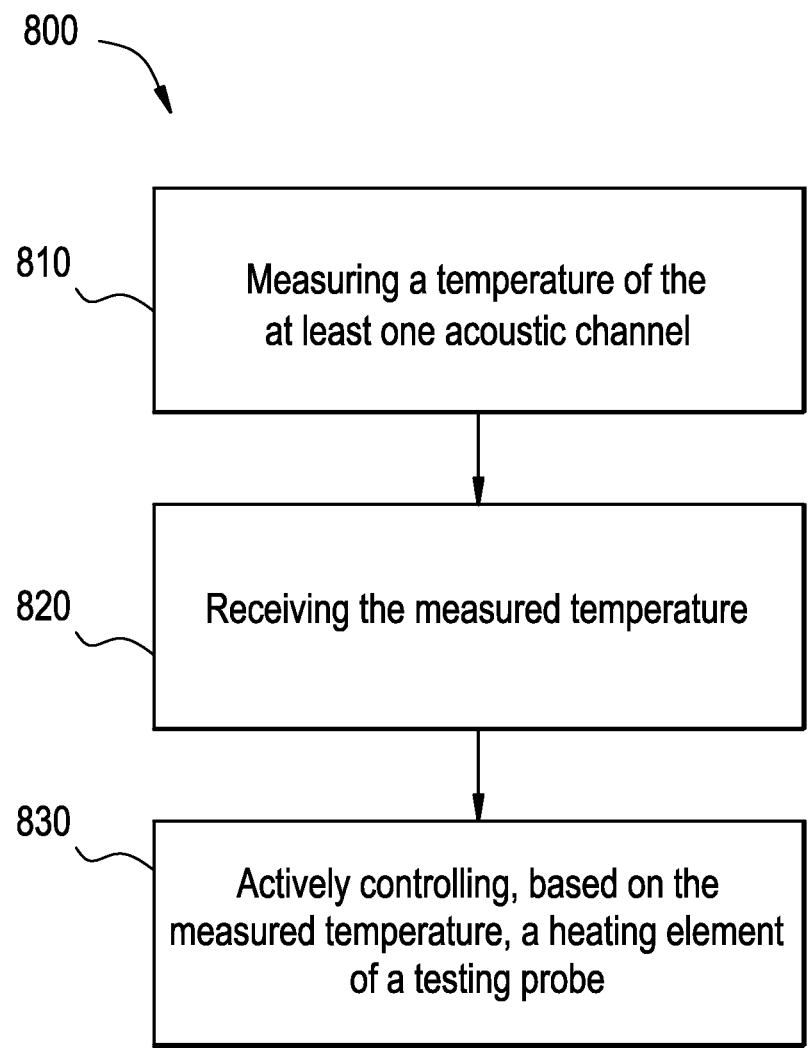

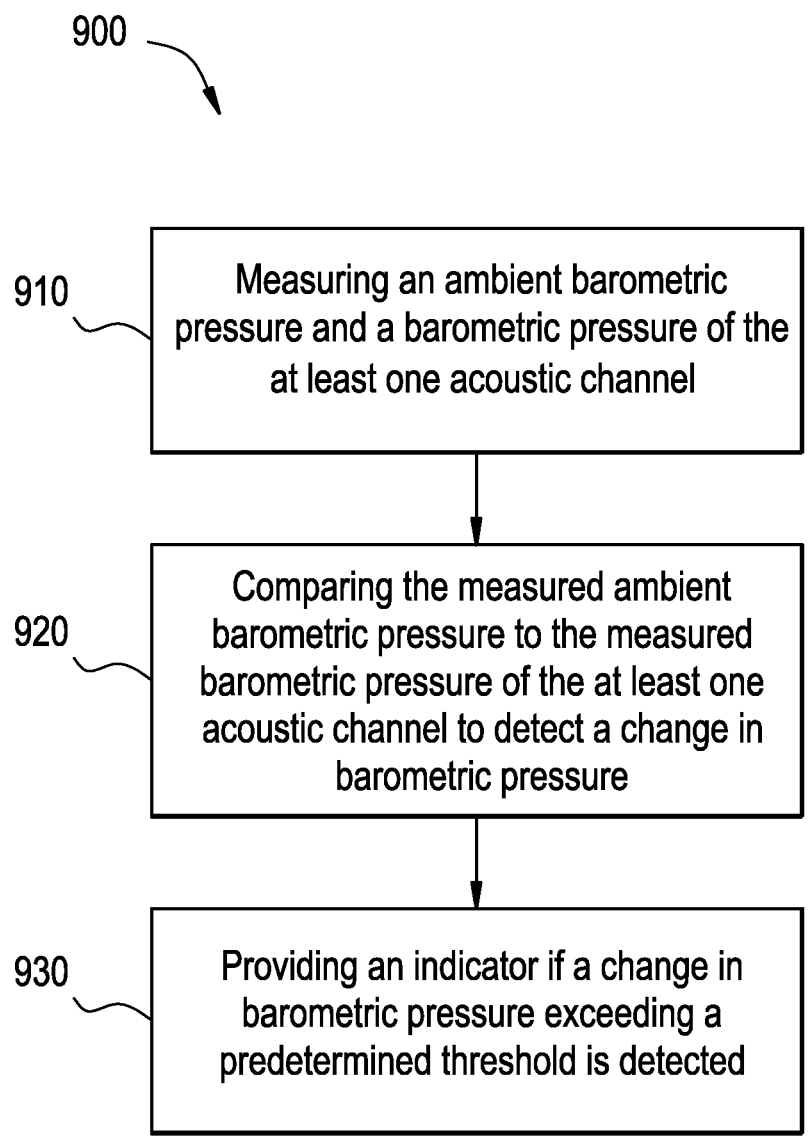

HEARING TESTING PROBE WITH INTEGRATED TEMPERATURE AND HUMIDITY SENSORS AND ACTIVE TEMPERATURE CONTROL

CROSS-REFERENCE TO RELATED APPLICATIONS/INCORPORATION BY REFERENCE

The present application claims priority under 35 U.S.C. §119(e) to provisional application Ser. No. 61/592,359, filed on Jan. 30, 2012.

The above referenced provisional application is hereby incorporated herein by reference in its entirety.

FEDERALLY SPONSORED RESEARCH OR DEVELOPMENT

This invention was made with government support under contract number N00014-10-M-0267 awarded by the Office of Naval Research. The government has certain rights in the invention.

MICROFICHE/COPYRIGHT REFERENCE

[Not Applicable]

BACKGROUND OF THE INVENTION

The present invention relates generally to hearing testing probes placed within ear canals that are coupled to an instrument that monitors the condition within the ears. More specifically, the present invention provides a hearing testing probe with integrated sensor(s) configured to measure environmental conditions. The present invention further provides a hearing testing probe with integrated heating element(s) configured to provide active temperature control.

Hearing test devices that monitor the condition within a human ear are known. Such test devices generally require that the person performing the test (the "operator") place a test probe of the device within the ear canal of a test subject. Once the probe is placed properly within the ear canal, the operator activates the device, usually by pressing a button or the like. The device then emits test signals into the subject's ear through the probe in the ear canal. In response to the test signals emitted, the device receives response signals from the ear, likewise through the probe in the ear canal. Such response signals received are then used to determine whether the ear is functioning properly.

Audiological testing for hearing impairment commonly requires an acoustic, air pressure, and/or vibratory stimulus to be presented to the test subject. Several of the methods for hearing evaluation require the use of a probe to generate and couple the stimulus directly to the subject's ear canal. Examples of hearing tests using these probes include optoacoustic emissions, acoustic immittance, acoustic reflex, reflectance, and, in some cases, auditory brainstem response. For each of these tests, certain characteristics of the stimulations need to be applied accurately in order to provide an accurate evaluation of the results.

In order to provide an accurate evaluation of the results, frequency response, magnitude, distortion, and other characteristics of the stimulus should be presented appropriately and measured accurately. However, environmental conditions, such as varying humidity levels, temperatures, and barometric pressures, for example, typically found in human ear canals can cause performance changes in microphone and speaker components commonly used in hearing testing probes.

An exemplary problem encountered when using existing hearing probes is the stability of the pressure response relative to the environmental humidity. The materials typically used in the diaphragms of certain types of microphones are hydroscopic, causing a shift in pressure sensitivity corresponding to changes in humidity. The change in sensitivity is often in the range of 0.02 to 0.06 dB per percent change in humidity. The change in sensitivity creates a difference between the calibrated and measured acoustic levels indicated by the microphone. This error adds a degree of uncertainty to the measurements.

Another problem encountered when using existing hearing probes is the risk of condensation on the internal components of the transducer(s). The high humidity levels commonly found in the ear canal can cause condensation to develop on the colder probe elements. This condensation may cause minerals or dirt to be irrecoverably deposited and cause a permanent and degrading change in performance of the transducer.

Barometric pressure at a given location typically changes no more than 3% from day to day. However, a system calibrated at one altitude and then put into service at a location of a different altitude may not provide the intended or indicated stimulus or measurement. The barometric pressure difference between sea level and a high-altitude location, such as La Paz, Columbia at roughly 12,000 ft. above sea level, can result in an apparent increase in the volume of the ear canal, as measured by the probe, by as much as 60%. This apparent change in volume could cause a 4 dB reduction in stimulus and measurement levels if a correction is not applied.

Hearing tests commonly rely on the coupling of stimulus into the inner ear, and some hearing tests also require a measurement of corresponding emissions from the ear to make proper diagnostic determinations. A seal to the ear canal is typically desired or required to properly perform the test function. During the insertion of the eartip to the ear canal, the air in the ear canal may be compressed. This pressure differential may cause a shift in the apparent stiffness of the tympanic membrane, causing a change in the conduction of the stimulus and emissions from the middle ear to the ear canal, adversely affecting the accuracy of the hearing test.

Further limitations and disadvantages of conventional and traditional approaches will become apparent to one of skill in the art, through comparison of such systems with some aspects of the present invention as set forth in the remainder of the present application.

BRIEF SUMMARY OF THE INVENTION

Certain embodiments provide a hearing testing probe with integrated sensor(s) configured to measure environmental conditions, substantially as shown in and/or described in connection with at least one of the figures, as set forth more completely in the claims.

Various embodiments provide a method for correcting a transducer response in a hearing testing system comprising a testing probe that comprises a transducer coupled with an acoustic channel, substantially as shown in and/or described in connection with at least one of the figures, as set forth more completely in the claims.

Certain embodiments provide a hearing testing probe with integrated heating element(s) configured to provide active temperature control, substantially as shown in and/or described in connection with at least one of the figures, as set forth more completely in the claims.

Various embodiments provide a method for actively controlling a temperature of a testing probe comprising a transducer coupled with an acoustic channel, substantially as shown in and/or described in connection with at least one of the figures, as set forth more completely in the claims.

Certain embodiments provide a method for indicating an elevated barometric pressure in an ear canal, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

BRIEF DESCRIPTION OF THE DRAWING(S)

FIG. 7 is a flow diagram that illustrates an exemplary method for correcting at least one transducer response in a hearing testing system comprising a testing probe that comprises at least one transducer coupled with at least one acoustic channel in accordance with an embodiment of the present technology.

FIG. 8 is a flow diagram that illustrates an exemplary method for actively controlling a temperature of a testing probe comprising at least one transducer coupled with at least one acoustic channel in accordance with an embodiment of the present technology.

FIG. 9 is a flow diagram that illustrates an exemplary method for indicating an elevated barometric pressure in an ear canal in accordance with an embodiment of the present technology.

Figure 1:
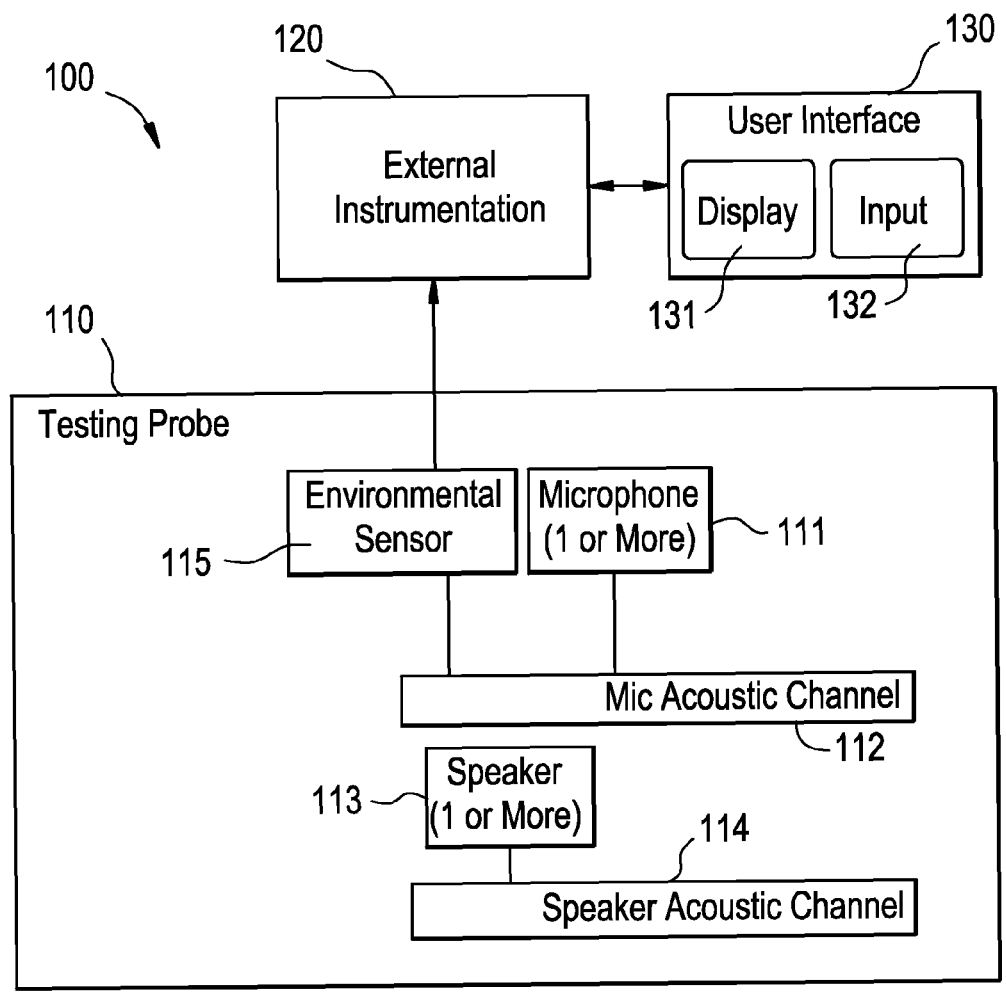
FIG. 1 illustrates a block diagram of an exemplary hearing testing system comprising a hearing testing probe with integrated environmental sensor(s) used in accordance with an embodiment of the present technology.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

Embodiments of the present technology provide a hearing testing probe with integrated sensor(s) configured to measure environmental conditions. Embodiments of the present technology provide a hearing testing probe with integrated heating element(s) configured to provide active temperature control.

Various embodiments provide a hearing testing system 100 comprising one or more transducers 111, 113, one or more environmental sensors 115, and one or more processors 118, 120. The transducer(s) 111, 113 are coupled with one or more acoustic channels 112, 114. The environmental sensor(s) 115 are coupled to the acoustic channel(s) 112, 114 and are configured to measure one or more environmental condition(s) of the acoustic channel(s) 112, 114. The processor(s) 118, 120 are coupled to the environmental sensor(s) 115. The processor(s) 118, 120 are configured to receive the measured environmental condition(s) from the environmental sensor(s) 115, and apply, based on the measured environmental condition, correction data 141, 142 to one or more transducer responses to generate one or more corrected transducer responses.

Certain embodiments provide a method 700 for correcting one or more transducer responses in a hearing testing system 100 comprising a testing probe 110 that comprises one or more transducers 111, 113 coupled with one or more acoustic channels 112, 114. The method 700 comprises measuring 710, by one or more environmental sensors 115 coupled to the acoustic channel(s) 112, 114, one or more environmental conditions of the acoustic channel(s) 112, 114. The method 700 comprises receiving 720, by the processor(s) 118, 120 coupled to the environmental sensor(s) 115, the measured environmental condition(s) from the environmental sensor(s) 115. The method 700 comprises applying 730, by the processor(s) 118, 120 and based on the measured environmental condition(s), correction data 141, 142 to one or more transducer responses to generate one or more corrected transducer responses.

Various embodiments provide a hearing testing system 100 comprising one or more transducers 111, 113, one or more environmental sensors 115, one or more heating elements 116, and one or more processors 118, 120. The transducer(s) 111, 113 are coupled with one or more acoustic channels 112, 114. The environmental sensor(s) 115 are coupled to the acoustic channel(s) 112, 114 and are configured to measure a temperature of the acoustic channel(s) 112, 114. The heating element(s) 116 are disposed in a testing probe 110 and are operable to heat the testing probe 110. The processor(s) 118, 120 are coupled to the environmental sensor(s) 115 and the heating element(s) 116. The processor(s) 118, 120 are configured to receive the measured temperature from the environmental sensor(s) 115, and actively control, based on the measured temperature, the heating element(s) 116.

Certain embodiments provide a method 800 for actively controlling a temperature of a testing probe 110 comprising one or more transducers 111, 113 coupled with one or more acoustic channels 112, 114. The method 800 comprises measuring 810, by one or more environmental sensors 115 coupled to the acoustic channel(s) 112, 114, a temperature of the acoustic channel(s) 112, 114. The method 800 comprises receiving 820, by processor(s) 118, 120 coupled to the environmental sensor(s) 115, the measured temperature from the environmental sensor(s) 115. The method 800 comprises actively controlling 830, by the processor(s) 118, 120 and based on the measured temperature, one or more heating elements 116 of the testing probe 110.

Various embodiments provide a method 900 for indicating an elevated barometric pressure in an ear canal. The method 900 comprises measuring 910 an ambient barometric pressure. The method comprises measuring 910, by one or more environmental sensors 115 coupled to one or more acoustic channels 112, 114 of a testing probe 110, a barometric pressure of the acoustic channel(s) 112, 114. The method 900 comprises comparing 920, by one or more processors 118, 120, the measured ambient barometric pressure to the measured barometric pressure of the acoustic channel(s) 112, 114 to detect a change in barometric pressure. The method 900 comprises providing 930 an indicator 117, 131 if a change in barometric pressure exceeding a predetermined threshold is detected.

FIG. 1 illustrates a block diagram of an exemplary hearing testing system 100 comprising a hearing testing probe 110 with integrated environmental sensor(s) 115 used in accordance with an embodiment of the present technology. FIGS. 2-6 illustrates a block diagram of an exemplary hearing testing system 100 comprising a hearing testing probe 110 with integrated environmental sensor(s) 115 and heating element(s) 116 used in accordance with an embodiment of the present technology.

Referring to FIGS. 1-6, a hearing testing system 100 comprises a testing probe 110, external instrumentation 120, and a user interface 130. The testing probe 110 can be directly or indirectly coupled to one or more of the external instrumentation 120 and the user interface 130, among other things. The testing probe 110 comprises transducers 111, 113, acoustic channels 112, 114, and environmental sensor(s) 115, for example.

Figure 2:
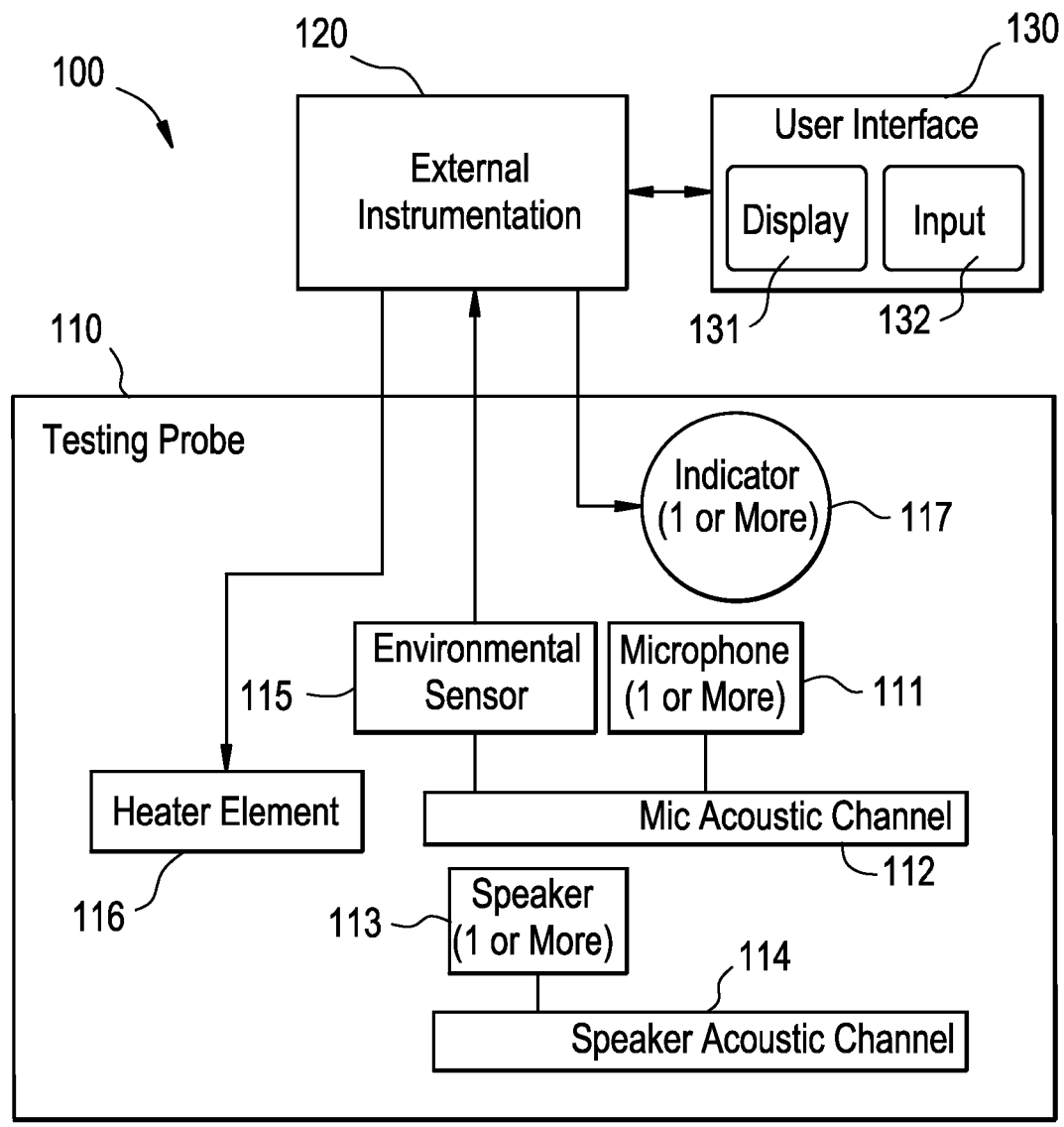
FIG. 2 illustrates a block diagram of an exemplary hearing testing system comprising a hearing testing probe with integrated environmental sensor(s) and heating element(s) used in accordance with an embodiment of the present technology.
Figure 3:
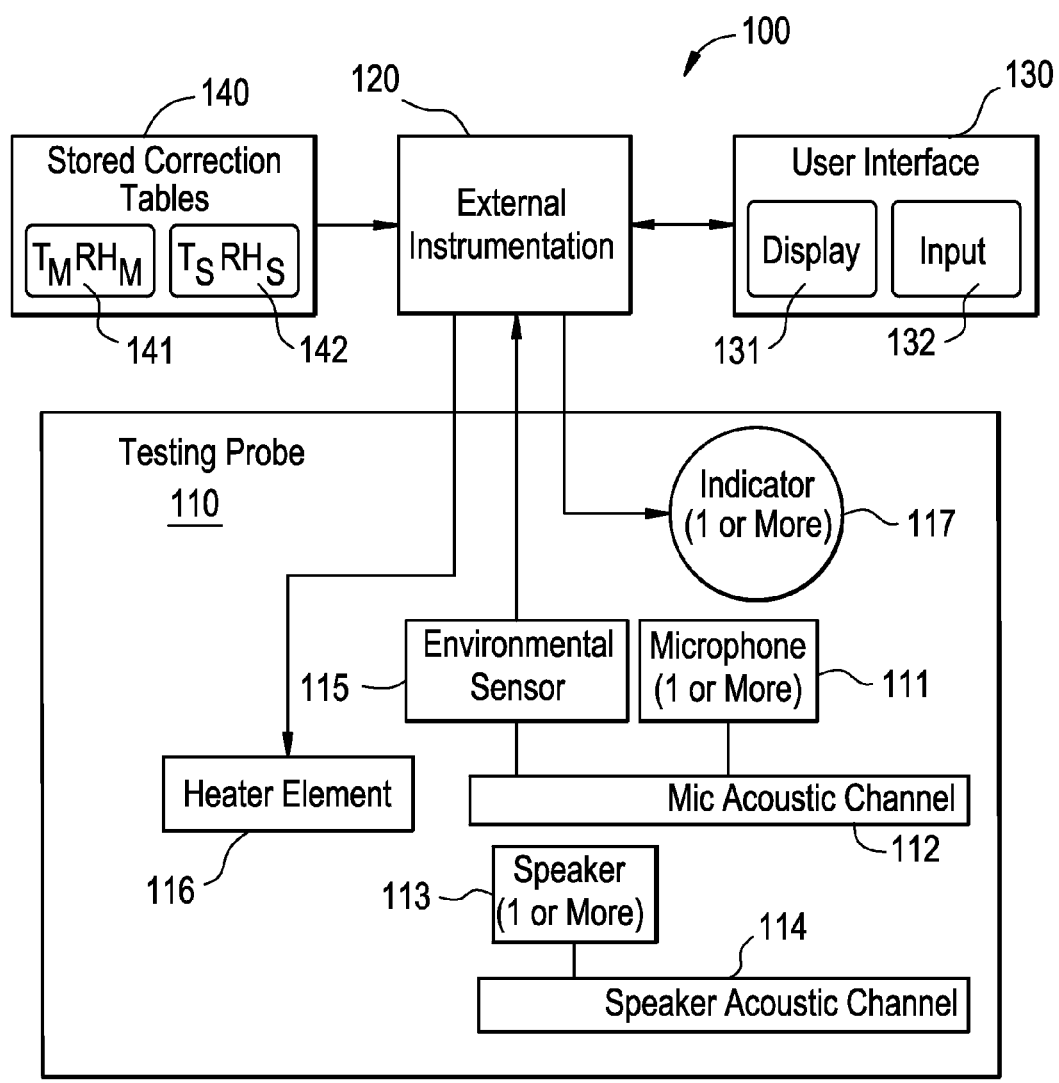
FIG. 3 illustrates a block diagram of an exemplary hearing testing system comprising a hearing testing probe with integrated environmental sensor(s) and heating element(s) used in accordance with an embodiment of the present technology.
Figure 4:
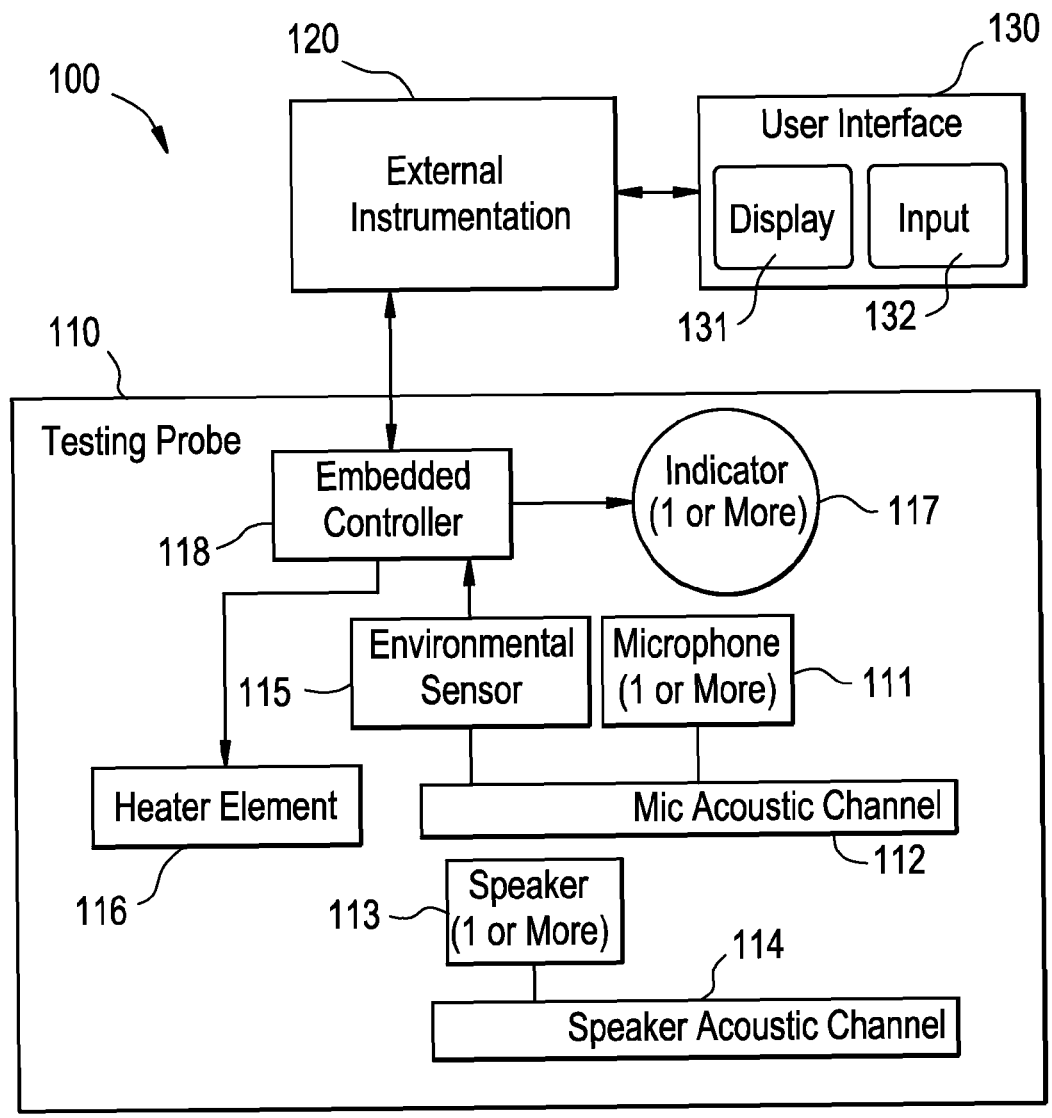
FIG. 4 illustrates a block diagram of an exemplary hearing testing system comprising a hearing testing probe with integrated environmental sensor(s) and heating element(s) used in accordance with an embodiment of the present technology.
Figure 5:
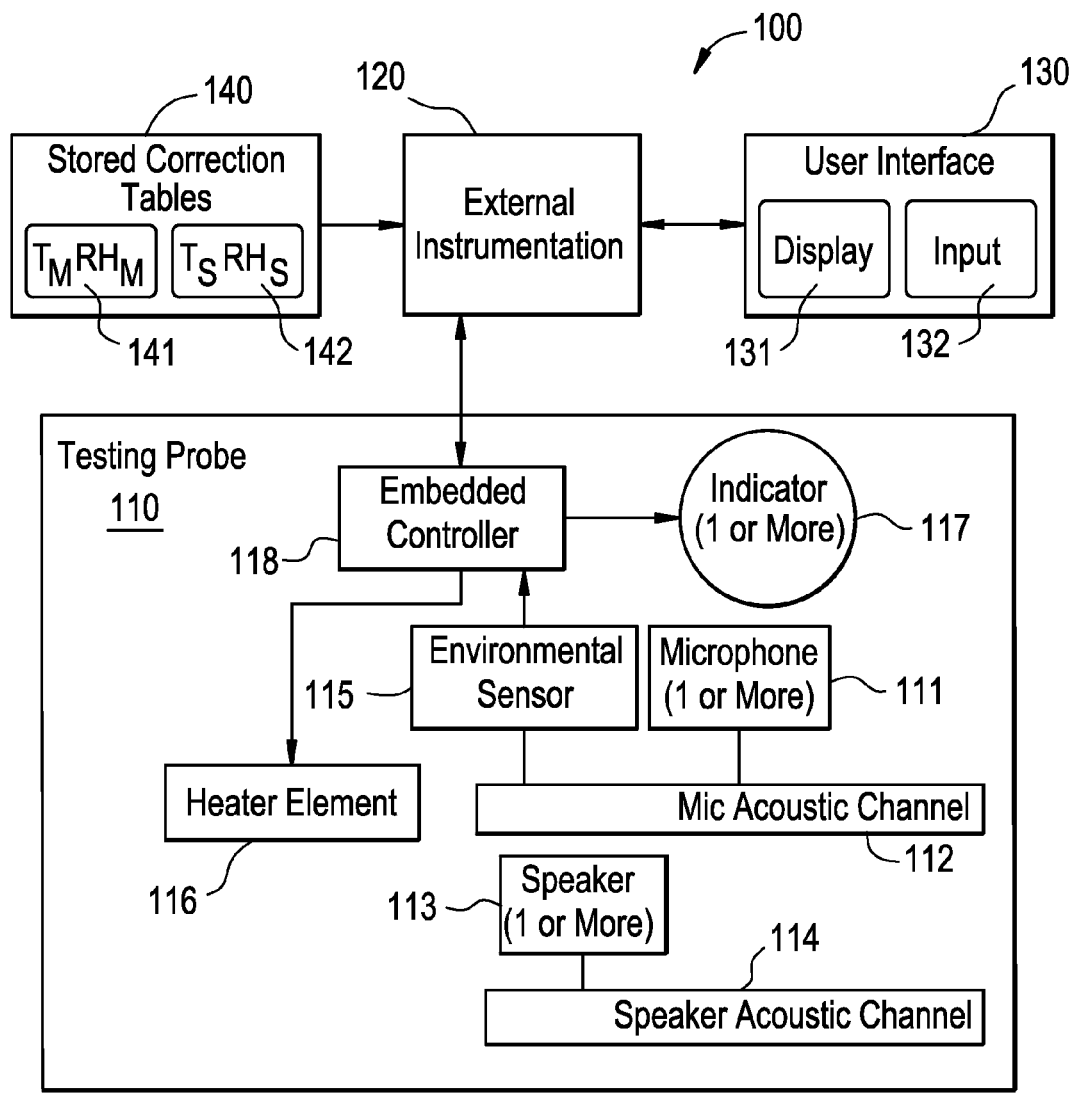
FIG. 5 illustrates a block diagram of an exemplary hearing testing system comprising a hearing testing probe with integrated environmental sensor(s) and heating element(s) used in accordance with an embodiment of the present technology.
Figure 6:
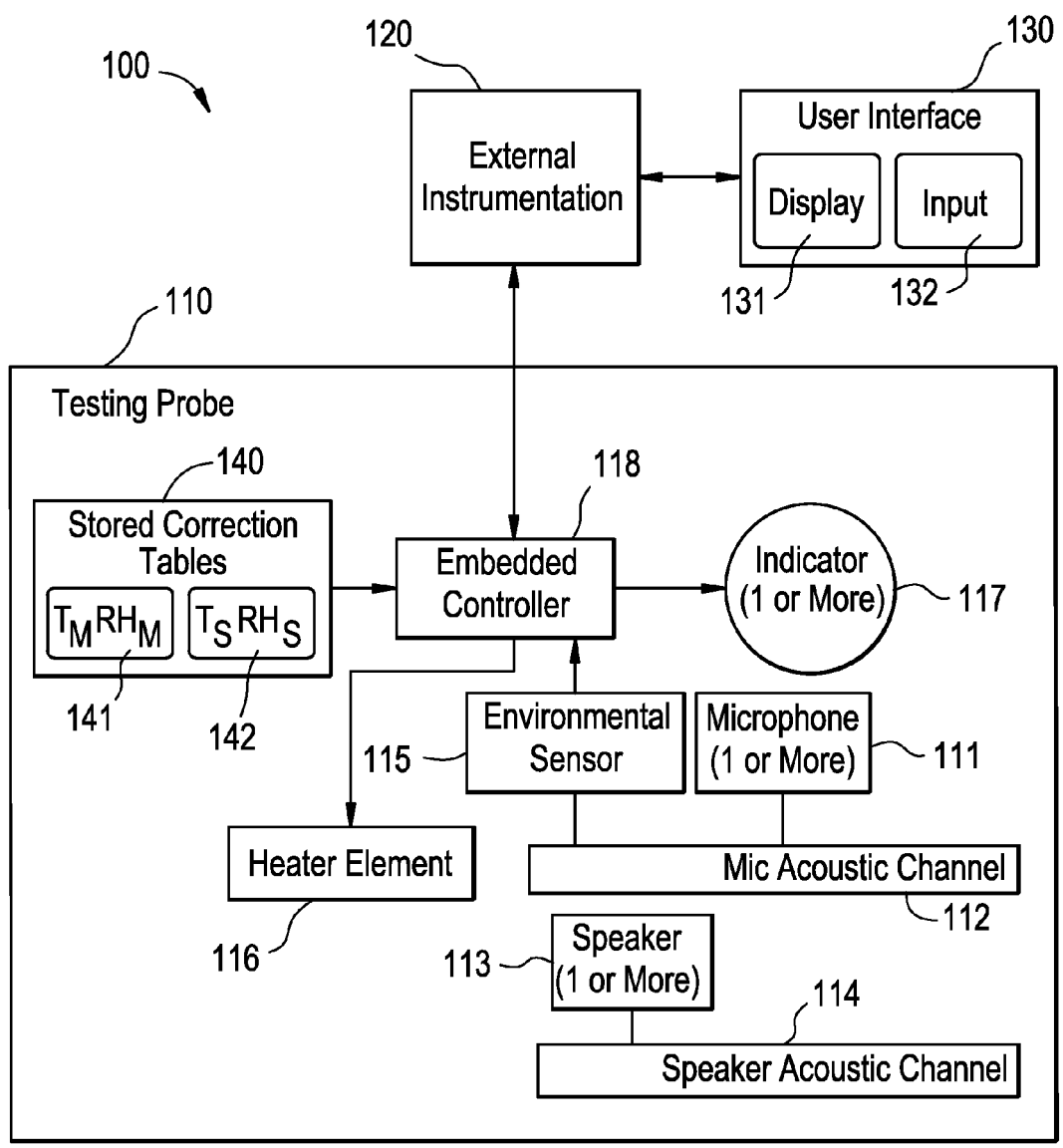
FIG. 6 illustrates a block diagram of an exemplary hearing testing system comprising a hearing testing probe with integrated environmental sensor(s) and heating element(s) used in accordance with an embodiment of the present technology.

The transducers 111, 113 can include one or more microphones 111 and one or more speakers 113. The microphone(s) 111 can be configured to convert acoustic energy received in one or more microphone acoustic channels 112 to electrical energy that is provided to external instrumentation 120, as illustrated in FIGS. 1-3, and/or to an embedded controller 118, as illustrated in FIGS. 4-6. The microphone(s) may be dynamic, condenser (externally or pre-polarized), piezo ceramic, silicon, or any suitable microphone, for example. The speaker(s) 113 may be configured to convert electrical energy received from external instrumentation 120, as illustrated in FIGS. 1-3, and/or to an embedded controller 118, as illustrated in FIGS. 4-6, into acoustic energy that is provided to one or more speaker acoustic channels 114. The speaker(s) 113 can be dynamic, balanced armature, or any suitable speaker, for example.

The acoustic channels 112, 114 may include one or more microphone acoustic channels 112 and one or more speaker acoustic channels 114. The microphone acoustic channel(s) 112 are operable to direct sound from an ear canal to the microphone(s) 111. The speaker acoustic channel(s) 114 are operable to direct sound generated by the speaker(s) to an ear canal. In various embodiments, the acoustic channels 112, 114 may be provided in a sound tube coupled to a detachable eartip, for example.

The environmental sensor(s) 115 may be any device capable of measuring an environmental condition. An environmental condition may include any suitable air quality measurement, such as air temperature, relative humidity, and/or barometric pressure, for example. Sound pressure level is not considered an environmental condition measured by environmental sensor(s) 115. Instead, sound pressure level and/or acoustic energy is measured by microphone(s) 111, for example. The environmental sensor(s) 115 may be resistive-based, capacitive-based, or any suitable environmental sensor(s). The environmental sensor(s) 115 can be analog and/or digital sensor(s), for example.

In various embodiments, the environmental sensor(s) 115 are configured to measure environmental condition(s) in one or more of the acoustic channels 112, 114. For example, an environmental sensor 115 may be coupled directly to a microphone acoustic channel 112 such that the temperature, relative humidity and/or barometric pressure proximate the microphone 111 can be measured. Additionally and/or alternatively, an environmental sensor 115 can be coupled directly to a speaker acoustic channel 114 such that the temperature, relative humidity and/or barometric pressure proximate the speaker 112 can be measured. In certain embodiments, the environmental condition(s) measurement data can be provided, substantially in real-time, to the external instrumentation 120, as illustrated in FIGS. 1-3, the display 131, and/or an embedded controller 118, as illustrated in FIGS. 4-6, for example. In various embodiments, an electronic compensation of the in-situ pressure sensitivity may be provided by the external instrumentation 120 and/or an embedded controller 118 based on a substantially instantaneous measurement of environmental characteristics, by the environmental sensor(s) 115, to which the hearing testing probe 110 is exposed.

The external instrumentation 120 may comprise one or more central processing units, microprocessors, microcontrollers, and/or the like. For example, the external instrumentation 120 may be a personal computer or an embedded microcontroller of a dedicated instrument, among other things. The external instrumentation 120 may be an integrated component, or may be distributed across various locations, for example. The external instrumentation 120 may be capable of receiving, processing and/or storing microphone, speaker, sensor and/or heating element information, as discussed below. The external instrumentation 120 can be capable of receiving input information from a user input device 132 and generating an output displayable by a display 131, among other things. In various embodiments, the external instrumentation 120 may apply correction factors retrieved from a memory 140 to one or more microphone responses and/or one or more speaker responses based on environmental condition(s) measurement data received from the environmental sensor(s) 115, as discussed below.

Referring to FIGS. 4-6, certain embodiments provide that the testing probe 110 comprises an embedded controller 118. The embedded controller 118 may be one or more central processing units, microprocessors, microcontrollers, and/or the like. The embedded controller 118 may be capable of receiving, processing and/or storing microphone, speaker, sensor and/or heater element information, as discussed below. In certain embodiments, the embedded controller 118 can be capable of providing testing probe information to external instrumentation 120, and receiving operating instructions and hearing test information from the external instrumentation 120, for example. The embedded controller 118 may be capable of controlling various components of the testing probe 110, such as the microphone 111, speaker, a heating element 116, and an indicator 117, among other things. In various embodiments, the embedded controller 118 may apply correction factors retrieved from a memory 140 to one or more microphone responses and/or one or more speaker responses, as illustrated in FIG. 6 and discussed below.

Referring again to FIGS. 1-6, the user interface 130 can be directly or indirectly coupled to, or integrated with, the external instrumentation 120. The user interface 130 may comprise a display 131 and a user input device 132. The display 131 may be any device capable of communicating visual information to a user. For example, a display 131 may include a fluorescent tube display, a liquid crystal diode display, a light emitting diode display, an organic light emitting diode display, and/or any suitable display. The display 131 can be operable to display information from testing probe 110 and/or external instrument 120, among other things. In various embodiments, the display 131 may display hearing test results, temperature measurements, humidity measurements, barometric pressure measurements, and/or any suitable information.

The user input device(s) 132 may include any device(s) capable of communicating information from a user and/or at the direction of the user to the external instrumentation 120 and/or testing probe 110, for example. The user input device(s) 132 may include button(s), a touchscreen, motion tracking, voice recognition, a mousing device, keyboard, and/or any other device capable of receiving a user directive. In certain embodiments, one or more of the user input devices 132 may be integrated into other components, such as the display 131, for example. As an example, user input device 132 may include a touchscreen display.

Referring to FIGS. 3, 5 and 6, certain embodiments provide that the hearing testing system 100 comprises a memory 140. The memory 140 may be one or more computer-readable memories, for example, such as a hard disk, floppy disk, CD, CD-ROM, DVD, compact storage, flash memory, random access memory, read-only memory, electrically erasable and programmable read-only memory and/or any suitable memory. The memory 140 may include databases, libraries, tables, or other storage accessed by and/or incorporated with the external instrumentation 120 and/or an embedded controller 118, for example. The memory 140 may be able to store data temporarily or permanently, for example.

Various embodiments provide that the memory 140 stores correction data 141, 142. For example, the memory 140 may store microphone correction data 141 and speaker correction data 142. In various embodiments, the correction data 141, 142 may be a correction factor based on a characteristic response of the microphone(s) 111 and/or speaker(s) 113 in temperature, relative humidity, and/or barometric pressure conditions. The characteristic response may be based on a nominal performance of the sensitivity of the transducers 111, 113 to temperature, relative humidity, and/or barometric pressure, for example. The nominal performance of the transducer sensitivity may be indicated by manufacturer specifications, an average of sample or production measurements, and/or a measurement of the transducers 111, 113 built into a particular testing probe 110, for example. The correction factors 141, 142 may be stored in memory 140 at the time of manufacture or calibration, for example, to be read and applied by the external instrumentation 120 and/or an embedded controller 118 during a hearing test.

In various embodiments, a correction factor 141, 142 may be generated based upon the measured sensitivity response in two or more discrete temperature, relative humidity, and/or barometric pressure conditions. The correction factor 141, 142 can be applied to the response of microphone(s) 111 and/or speaker(s) 113 as a linear fit correction, for example. In various embodiments, application of the correction factor 141, 142 by one or more of the external instrumentation 120 or embedded controller 118 may reduce a theoretical change of transducer pressure sensitivity from as much as 6 dB or more to a compensated 2 dB or less over operating temperature and humidity extremes, nominally +15 degrees Celsius to +35 degrees Celsius and 10% to 90% relative humidity, for example.

In certain embodiments, the correction data 141, 142 may be stored as a lookup table corresponding to a series of measurements of the sensitivity of the transducers 111, 113 through a range of temperatures, relative humidities, and/or barometric pressures, for example. The sensitivity measurements may be used directly for correction of the transducer response, or may be interpolated to create a correction factor for a specific level of temperature, relative humidity, and/or barometric pressure, among other things. In certain embodiments, the sensitivity measurements can be mapped using a polynomial or other curvilinear regression analysis to create a non-linear equation for correction across a range of sensitivity measurements.

Certain embodiments provide that the hearing testing system 100 can programmatically determine the existence of an ear canal at the entrance of the hearing test probe 110 to provide automatic operation or verification, among other things. For example, the environmental sensor(s) 115 can measure the temperature, relative humidity, and/or barometric pressure in an acoustic channel 112, 114 for comparison with measured ambient temperature, relative humidity, and/or barometric pressure. The external instrumentation 120, embedded controller 118, or the like, can detect that the testing probe 110 has been inserted in an ear canal by determining that a difference between measured environmental conditions in an acoustic channel 112, 114 and ambient environmental conditions exceed a pre-determined threshold, for example. In certain embodiments, the user interface display 131 can display information regarding whether testing probe 110 insertion is detected. In various embodiments, an indicator 117 of the testing probe 110 may be activated when testing probe 110 insertion is detected. In certain embodiments, other methods of detecting insertion of a testing probe 110 in an ear canal, such as acoustic and/or air pressure methods of detection, for example, may be used in conjunction with determining the difference between acoustic channel 112, 114 and ambient environmental conditions to improve insertion detection accuracy and/or to detect a proper seal, among other things.

Referring to FIGS. 2-6, certain embodiments provide one or more heating element(s) disposed within a body of the hearing test probe 110. The heating element(s) may be any device capable of generating heat energy and transferring the heat energy to the hearing test probe 110. The heating element(s) 116 may be comprised of an electrically resistive material that converts electrical energy into thermal energy. For example, the electrically resistive material can be a thick-film, thin-film, carbon, and/or wire-wound resistor. As another example, the electrically resistive material may be resistive elements in the form of etched traces on a variety of substrates. In various embodiments, any suitable form of heating element may be used. The heating element(s) 116 are mounted in the hearing test probe 110 in a manner that provides short thermal paths to the microphone(s) 111, speaker(s) 113, and environmental sensor(s) 115.

The heating element 116 may provide the hearing testing probe 110 an elevated temperature relative to the ambient temperature. An elevated temperature could prevent condensation on transducer 111, 113 elements in the hearing test probe 110 when exposed to high humidity environments, particularly as found in mammalian ear canals. By raising the temperature of the hearing testing probe 110 to be near the temperature of the ear canal, the temperature gradient that would cause condensation in the hearing test probe 110 can be eliminated.

In various embodiments, the external instrumentation 120 and/or the embedded controller 118 may actively control the heating element(s) 116 to maintain a desired temperature based on temperature measurements of the environmental sensor(s) 115. For example, the temperature may be maintained using the feedback from the environmental sensor(s) 115 to control the application of electrical energy to the heating element 116. The active control of the probe temperature provides a maintained probe temperature at a selected elevated temperature irrespective of the ambient temperature. In certain embodiments, the temperature may be maintained consistently while the hearing testing system 100 is active or may be activated when a hearing test procedure is in process. For example, the heating element(s) 116 can be activated when the probe is coupled to an ear canal, which may be determined through either automated detection or by a manual indication provided by a user of the hearing testing system 100, among other things. In various embodiments, the heating element(s) 116 may be used to substantially match the temperature of the probe 110 to the temperature of an ear canal as measured by the environmental sensor(s) 115. Substantially matching the hearing testing probe 110 temperature to an ear canal temperature may minimize a change in microphone pressure sensitivity between the ambient environment and the environment of the sealed ear canal, for example.

Certain embodiments provide calibrating and performing hearing test functions using the testing probe 110 heated to substantially the same temperature. Performing hearing test functions using the testing probe 110 heated to substantially the same temperature that the testing probe was calibrated at can minimize measurement errors caused by sensitivity shifts.

Referring to FIGS. 2-6, certain embodiments provide that the testing probe 110 comprises one or more indicators 117. The indicator(s) 117 can be any indicator on a testing probe 110 capable of providing information to a user of the testing probe 110. For example, the indicator(s) 117 may be visual indicators, audible indicators, or any suitable indicator or combination of indicators. Visual indicator(s) can include light emitting diodes, lamps, or any suitable visual indicator. Audible indicators may include tones, voice messages, or any suitable audible indicator. In various embodiments, the indicator 117 provides an indication when predetermined probe conditions, such as temperature conditions, probe insertion detection conditions, or any suitable conditions, are satisfied. For example, a hearing testing system 100 that detects that the testing probe 110 is sealed in an ear canal can provide an indication to that effect by activating a light emitting diode or sequence of light emitting diodes, among other things.

In certain embodiments, increasing the temperature of the hearing testing probe 110 may also be used to decrease the level of discomfort for a subject of a hearing test. In various embodiments, increasing the temperature of the hearing testing probe 110 can also limit or eliminate the startle effect of a cold hearing test probe 110 when applied to a newborn or infant, particularly when it is deemed beneficial that the newborn or infant be asleep during the test, and waking the newborn or infant on application of the hearing test probe 110 would be not desirable.

FIG. 7 is a flow diagram that illustrates an exemplary method 700 for correcting at least one transducer response in a hearing testing system 100 comprising a testing probe 110 that comprises at least one transducer 111, 113 coupled with at least one acoustic channel 112, 114 in accordance with an embodiment of the present technology. Referring to FIG. 7, at step 710, one or more environmental conditions of one or more acoustic channel(s) 112, 114 may be measured by one or more environmental sensors 115 coupled to the acoustic channel(s) 112, 114. At step 720, the measured environmental condition(s) from the environmental sensor(s) 115 can be received by the external instrumentation 120 and/or the embedded controller 118, for example. At step 730, based on the measured environmental condition(s), the external instrumentation 120 and/or the embedded controller 118 may apply correction data 141, 142 to one or more transducer responses to generate one or more corrected transducer responses.

In various embodiments, the environmental condition(s) comprise barometric pressure and the correction data 141, 142 corresponds to a change in altitude correction. In certain embodiments, the environmental condition(s) comprise relative humidity and the correction data 141, 142 corresponds to a relative humidity correction applied to the transducer response(s) to generate the corrected transducer response(s). In various embodiments, the external instrumentation 120 and/or the embedded controller 118 can detect whether the testing probe 110 is inserted in an ear canal based on a determined difference between the measured environmental condition(s) and one or more corresponding ambient environmental conditions. Although the method is described with reference to the exemplary elements of the systems described above, it should be understood that other implementations are possible.

One or more of the steps of the method 700 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps, and/or perform the steps in a different order than the order listed, and/or combine certain of the steps listed above. For example, some steps may not be performed in certain embodiments of the present invention. As a further example, certain steps may be performed in a different temporal order, including simultaneously, than listed above.

FIG. 8 is a flow diagram that illustrates an exemplary method 800 for actively controlling a temperature of a testing probe 110 comprising at least one transducer 111, 113 coupled with at least one acoustic channel 112, 114 in accordance with an embodiment of the present technology. Referring to FIG. 8, at step 810, a temperature of one or more acoustic channels 112, 114 may be measured by one or more environmental sensors 115 coupled to the acoustic channel(s) 112, 114. At step 820, the measured temperature from the environmental sensor(s) 115 can be received by the external instrumentation 120 and/or the embedded controller 118, for example, coupled to the environmental sensor(s) 115. At step 830, based on the measured temperature, the external instrumentation 120 and/or the embedded controller 118 can actively control one or more heating element(s) 116 of the testing probe 110.

In certain embodiments, in response to the measured temperature, the external instrumentation 120 and/or the embedded controller 118 actively controls the heating element(s) 116 to substantially maintain a pre-defined temperature of the testing probe 110 and/or a pre-defined temperature range of the testing probe 110. The pre-defined temperature of the testing probe 110 and/or the pre-defined temperature range of the testing probe 110 can be pre-defined in firmware of the processor(s) 118, 120 and/or selected using a user interface 130 coupled to the processor(s) 118, 120, for example. In various embodiments, during a hearing test procedure and/or after the testing probe 110 is coupled to an ear canal, the external instrumentation 120 and/or the embedded controller 118 may activate the heating element(s) 116. The external instrumentation 120 and/or the embedded controller 118 can detect that the testing probe 110 is coupled to the ear canal based on a determined difference between the measured temperature and an ambient temperature, for example. Although the method is described with reference to the exemplary elements of the systems described above, it should be understood that other implementations are possible.

One or more of the steps of the method 800 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps, and/or perform the steps in a different order than the order listed, and/or combine certain of the steps listed above. For example, some steps may not be performed in certain embodiments of the present invention. As a further example, certain steps may be performed in a different temporal order, including simultaneously, than listed above.

FIG. 9 is a flow diagram that illustrates an exemplary method for indicating an elevated barometric pressure in an ear canal in accordance with an embodiment of the present technology. Referring to FIG. 9, at step 910, an ambient barometric pressure and a barometric pressure of one or more acoustic channels 112, 114 may be measured. For example, one or more environmental sensors 115 coupled to the acoustic channel(s) 112, 114 can measure the barometric pressure of the acoustic channel(s) 112, 114. An ambient environmental sensor (not shown) may be included in the testing probe 110, external instrumentation 120, or any suitable location for measuring ambient barometric pressure. At step 920, the measured ambient barometric pressure and the measured acoustic channel barometric pressure can be compared to detect a change in barometric pressure. At step 930, if a change in the barometric pressure exceeds a predetermined threshold, an indication may be provided to a user at a user interface display 131, testing probe indicator 117, or any suitable indication mechanism. Although the method is described with reference to the exemplary elements of the systems described above, it should be understood that other implementations are possible.

One or more of the steps of the method 900 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps, and/or perform the steps in a different order than the order listed, and/or combine certain of the steps listed above. For example, some steps may not be performed in certain embodiments of the present invention. As a further example, certain steps may be performed in a different temporal order, including simultaneously, than listed above.

Various embodiments provide a hearing testing system 100 comprising one or more transducers 111, 113, one or more environmental sensors 115, and one or more processors 118, 120. The transducer(s) 111, 113 are coupled with one or more acoustic channels 112, 114. The environmental sensor(s) 115 are coupled to the acoustic channel(s) 112, 114 and are configured to measure one or more environmental condition(s) of the acoustic channel(s) 112, 114. The processor(s) 118, 120 are coupled to the environmental sensor(s) 115. The processor(s) 118, 120 are configured to receive the measured environmental condition(s) from the environmental sensor(s) 115, and apply, based on the measured environmental condition, correction data 141, 142 to one or more transducer responses to generate one or more corrected transducer responses.

In certain embodiments, the transducer(s) 111, 113 comprise one or more microphones 111 operable to receive acoustic energy in the acoustic channel(s) 112 and convert the acoustic energy to the transducer response(s).

In various embodiments, the transducer(s) 111, 113 comprise one or more speakers 113 operable to receive the corrected transducer response(s) and convert the corrected transducer response(s) to acoustic energy provided in the acoustic channel(s) 114.

In certain embodiments, the hearing testing system 100 comprises a testing probe 110 that comprises the transducer(s) 111, 113, the environmental sensor(s) 115, and the acoustic channel(s) 112, 114.

In various embodiments, the processor(s) 118, 120 are integrated with external instrumentation 120 operable to perform a hearing test using the testing probe 110.

In certain embodiments, the testing probe 110 comprises the processor(s) 118.

In various embodiments, the environmental condition is air temperature, relative humidity, and/or barometric pressure.

In certain embodiments, the hearing testing system 100 comprises a display 131 operable to display the measured environmental condition(s).

In various embodiments, the hearing testing system 100 comprises a memory 140 configured to store the correction data 141, 142. The correction data comprises one or more of microphone correction data 141 and speaker correction data 142.

In certain embodiments, the correction data 141, 142 comprises one or more correction factors based on a characteristic response at a plurality of environmental conditions for one or more of the transducer(s) 111, 113, a same type as the transducer(s) 111, 113 as indicated by a manufacturer specification, and sample transducers of the same type as the transducer(s) 111, 113, where the characteristic response is an average of the sample transducers.

In various embodiments, the correction factor(s) are applied by the processor(s) using one or more of a linear fit correction, a lookup table, and a non-linear equation generated using a curvilinear regression analysis.

In certain embodiments, the processor(s) 118, 120 are configured to determine a difference between the measured environmental condition(s) and one or more ambient environmental conditions to detect whether the testing probe 110 is inserted in an ear canal.

In various embodiments, the testing probe 110 comprises one or more indicators 117 configured to provide an indication when the testing probe 110 is inserted in an ear canal.

Certain embodiments provide a method 700 for correcting one or more transducer responses in a hearing testing system 100 comprising a testing probe 110 that comprises one or more transducers 111, 113 coupled with one or more acoustic channels 112, 114. The method 700 comprises measuring 710, by one or more environmental sensors 115 coupled to the acoustic channel(s) 112, 114, one or more environmental conditions of the acoustic channel(s) 112, 114. The method 700 comprises receiving 720, by the processor(s) 118, 120 coupled to the environmental sensor(s) 115, the measured environmental condition(s) from the environmental sensor(s) 115. The method 700 comprises applying 730, by the processor(s) 118, 120 and based on the measured environmental condition(s), correction data 141, 142 to one or more transducer responses to generate one or more corrected transducer responses.

In certain embodiments, the environmental condition(s) comprise barometric pressure and the correction data 141, 142 corresponds to a change in altitude correction.

In various embodiments, the environmental condition(s) comprise relative humidity and the correction data 141, 142 corresponds to a relative humidity correction applied to the transducer response(s) to generate the corrected transducer response(s).

In certain embodiments, the method 700 for correcting one or more transducer responses in the hearing testing system 100 comprises determining a difference between the measured environmental condition(s) and one or more ambient environmental conditions to detect whether the testing probe 110 is inserted in an ear canal.

Various embodiments provide a hearing testing system 100 comprising one or more transducers 111, 113, one or more environmental sensors 115, one or more heating elements 116, and one or more processors 118, 120. The transducer(s) 111, 113 are coupled with one or more acoustic channels 112, 114. The environmental sensor(s) 115 are coupled to the acoustic channel(s) 112, 114 and are configured to measure a temperature of the acoustic channel(s) 112, 114. The heating element(s) 116 are disposed in a testing probe 110 and are operable to heat the testing probe 110. The processor(s) 118, 120 are coupled to the environmental sensor(s) 115 and the heating element(s) 116. The processor(s) 118, 120 are configured to receive the measured temperature from the environmental sensor(s) 115, and actively control, based on the measured temperature, the heating element(s) 116.

In certain embodiments, the testing probe 110 comprises one or more indicators 117 configured to provide an indication when the measured temperature is substantially matched with a pre-defined temperature and/or within a pre-defined temperature range.

In various embodiments, the processor(s) 118, 120 actively control the heating element(s) 116 to substantially maintain a pre-defined temperature of the testing probe 110 and/or a pre-defined temperature range of the testing probe 110 in response to the measured temperature received from the environmental sensor(s) 115.

In certain embodiments, the processor(s) 118, 120 are configured to activate the heating element(s) 116 and control a temperature of the testing probe 110 during a hearing test procedure and/or after the testing probe 110 is coupled to an ear canal.

In various embodiments, the processor(s) 118, 120 are configured to detect that the testing probe 110 is coupled to the ear canal based on a determined difference between the measured temperature and an ambient temperature.

Certain embodiments provide a method 800 for actively controlling a temperature of a testing probe 110 comprising one or more transducers 111, 113 coupled with one or more acoustic channels 112, 114. The method 800 comprises measuring 810, by one or more environmental sensors 115 coupled to the acoustic channel(s) 112, 114, a temperature of the acoustic channel(s) 112, 114. The method 800 comprises receiving 820, by processor(s) 118, 120 coupled to the environmental sensor(s) 115, the measured temperature from the environmental sensor(s) 115. The method 800 comprises actively controlling 830, by the processor(s) 118, 120 and based on the measured temperature, one or more heating elements 116 of the testing probe 110.

In various embodiments, the actively controlling the heating element(s) 116 substantially maintains one or more of a pre-defined temperature of the testing probe 110 and a pre-defined temperature range of the testing probe 110 in response to measured temperature.

In certain embodiments, the pre-defined temperature of the testing probe 110 and/or the pre-defined temperature range of the testing probe 110 are pre-defined in firmware of the processor(s) 118, 120 and/or selected using a user interface 130 coupled to the processor(s) 118, 120.

In various embodiments, the method 800 for actively controlling the temperature of the testing probe 110 comprises activating, by the processor(s) 118, 120, the heating element(s) 116. The activating occurs during a hearing test procedure and/or after the testing probe 110 is coupled to an ear canal.

In certain embodiments, the method 800 for actively controlling the temperature of the testing probe 110 comprises detecting, by the processor(s) 118, 120, that the testing probe 110 is coupled to the ear canal based on a determined difference between the measured temperature and an ambient temperature.

Various embodiments provide a method 900 for indicating an elevated barometric pressure in an ear canal. The method 900 comprises measuring 910 an ambient barometric pressure. The method comprises measuring 910, by one or more environmental sensors 115 coupled to one or more acoustic channels 112, 114 of a testing probe 110, a barometric pressure of the acoustic channel(s) 112, 114. The method 900 comprises comparing 920, by one or more processors 118, 120, the measured ambient barometric pressure to the measured barometric pressure of the acoustic channel(s) 112, 114 to detect a change in barometric pressure. The method 900 comprises providing 930 an indicator 117, 131 if a change in barometric pressure exceeding a predetermined threshold is detected.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A hearing testing system comprising:
    a testing probe comprising:
        a sound tube comprising at least one acoustic channel, the sound tube coupled to an eartip configured for insertion into an ear canal,
        at least one transducer coupled with the at least one acoustic channel, and
        at least one environmental sensor coupled to the at least one acoustic channel, the at least one environmental sensor configured to measure at least one environmental condition of the at least one acoustic channel; and
    at least one processor coupled to the at least one environmental sensor, the at least one processor configured to:
        receive the at least one measured environmental condition from the at least one environmental sensor, and
        apply hearing test correction data corresponding with the at least one measured environmental condition to at least one hearing test transducer response to generate at least one corrected hearing test transducer response.

2. The apparatus of claim 1, wherein the at least one transducer comprises at least one microphone operable to receive acoustic energy in the at least one acoustic channel and convert the acoustic energy to the at least one transducer response.

3. The apparatus of claim 1, wherein the at least one transducer comprises at least one speaker operable to receive the at least one corrected hearing test transducer response and covert the at least one corrected hearing test transducer response to acoustic energy provided in the at least one acoustic channel.

4. The apparatus of claim 1, wherein the at least one processor is integrated with external instrumentation operable to perform a hearing test using the testing probe.

5. The apparatus of claim 1, wherein the testing probe comprises the at least one processor.

6. The apparatus of claim 1, wherein the environmental condition is at least one of air temperature, relative humidity, and barometric pressure.

7. The apparatus of claim 1, comprising a display operable to display the at least one measured environmental condition.

8. The apparatus of claim 1, comprising a memory configured to store the hearing test correction data corresponding to the at least one measured environmental condition, the hearing test correction data comprising at least one of microphone correction data and speaker correction data.

9. The apparatus of claim 1, wherein the hearing test correction data comprises at least one correction factor based on a characteristic response at a plurality of environmental conditions for at least one of:
  the at least one transducer,
  a same type as the at least one transducer as indicated by a manufacturer specification, and
  a plurality of sample transducers of the same type as the at least one transducer, wherein the characteristic response is an average of the plurality of sample transducers.

10. The apparatus of claim 9, wherein the at least one correction factor is applied by the at least one processor using at least one of:
  a linear fit correction,
  a lookup table, and
  a non-linear equation generated using a curvilinear regression analysis.

11. The apparatus of claim 1, wherein the at least one processor is configured to determine a difference between the at least one measured environmental condition and at least one ambient environmental condition to detect whether the testing probe is inserted in the ear canal.

12. The apparatus of claim 11, wherein the testing probe comprises at least one indicator configured to provide an indication when the testing probe is inserted in the ear canal.

13. A method for correcting at least one hearing test transducer response in a hearing testing system comprising a testing probe that comprises at least one transducer coupled with at least one acoustic channel of a sound tube, the sound tube coupled to an eartip configured for insertion into an ear canal, the method comprising:
  measuring, by at least one environmental sensor coupled to the at least one acoustic channel, at least one environmental condition of the at least one acoustic channel;
  receiving, by at least one processor coupled to the at least one environmental sensor, the at least one measured environmental condition from the at least one environmental sensor; and
  applying, by the at least one processor, hearing test correction data corresponding with the at least one measured environmental condition to the at least one hearing test transducer response to generate at least one corrected hearing test transducer response.

14. The method of claim 13, wherein the at least one environmental condition comprises barometric pressure, and wherein the hearing test correction data corresponds to a change in altitude correction.

15. The method of claim 13, wherein the at least one environmental condition comprises relative humidity, and wherein the hearing test correction data corresponds to a relative humidity correction applied to the at least one hearing test transducer response to generate the at least one corrected hearing test transducer response.

16. The method of claim 13, comprising determining a difference between the at least one measured environmental condition and at least one ambient environmental condition to detect whether the testing probe is inserted in the ear canal.

* * * * *